(12) United States Patent
Birk et al.

(10) Patent No.: US 7,223,961 B2
(45) Date of Patent: May 29, 2007

(54) DEVICE FOR SELECTIVELY DETECTING SPECIFIC WAVELENGTH COMPONENTS OF A LIGHT BEAM

(75) Inventors: Holger Birk, Meckesheim (DE); Volker Seyfried, Nussloch (DE); Rafael Storz, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 10/923,239

(22) Filed: Aug. 20, 2004

(65) Prior Publication Data

US 2005/0045812 A1    Mar. 3, 2005

Related U.S. Application Data

(60) Provisional application No. 60/563,117, filed on Apr. 16, 2004.

(30) Foreign Application Priority Data

Aug. 28, 2003   (DE) ................... 103 40 020

(51) Int. Cl.
*G01J 3/50* (2006.01)
*G01J 3/28* (2006.01)

(52) U.S. Cl. ..................................... 250/226; 356/326
(58) Field of Classification Search ............... 250/226, 250/208.1, 216, 237 G; 356/318–334
See application file for complete search history.

(56) References Cited

U.S. PATENT DOCUMENTS 5,014,121 A * 5/1991 Hasegawa et al. ............. 348/70
6,459,484 B1 * 10/2002 Yokoi ......................... 356/318

FOREIGN PATENT DOCUMENTS

DE     100 16 361 A1    10/2001
DE     10102033         8/2002

* cited by examiner

*Primary Examiner*—Thanh X. Luu
(74) *Attorney, Agent, or Firm*—Darby &* Darby

(57) ABSTRACT

A device for selectively detecting specific wavelength components of a light beam includes a spectral spreading element for spectrally spreading the light beam, and a detector array arranged downstream of the element. The detector array includes light-insensitive regions and light-sensitive regions. The element and the detector array are matched to each other so that selectable wavelength components of the light beam hit the light-insensitive regions and remaining wavelength components of the light beam hit the light-sensitive regions.

10 Claims, 6 Drawing Sheets

DEVICE FOR SELECTIVELY DETECTING SPECIFIC WAVELENGTH COMPONENTS OF A LIGHT BEAM

Priority is claimed to provisional application 60/563,117, filed Apr. 16, 2004, and to German patent application 103 40 020.6, filed Aug. 28, 2003, the entire disclosure of each of which is hereby incorporated by reference herein.

The present invention relates to a device for selectively detecting specific wavelength components of a light beam, including an element for spectrally spreading out the light beam and a detector array downstream of the element. The present invention further relates to a method for suppressing excitation lines in the detection light beam of a microscope, in particular for use in a fluorescence microscope, in which an element for spectrally spreading out the detection light beam and a detector array downstream of the element are disposed in the optical path of the detection light beam.

BACKGROUND

Devices for selectively detecting specific wavelength components of a light beam have been used in practice for quite some time, reference being made, just as an example, to German Patent Application DE 101 02 033 A1. FIG. 2 there shows a device, in which a light beam to be detected is spectrally split by a prism. A selection device in the form of a slit diaphragm is located downstream of the prism. Certain wavelength components are blocked by the slit diaphragm jaw while other wavelength components pass through the slit diaphragm and are detected in a first detector, while still other wavelength components are reflected by the slit diaphragm jaw by a totally reflecting coating and are then detected in a second detector. Having a multitude of components, this system is extremely complex and in addition not very flexible in terms of a changed composition of the spectral regions to be detected.

Methods for suppressing excitation lines in the detection light beam of a microscope are also used in practice. In the known methods, the excitation lines are generally blocked using special filters, for example, electro-optical filters, that have an absorbing effect for the wavelengths of the excitation lines. In this connection, it is a disadvantage that the absorption is generally not complete so that in spite of the filtering, there is still excitation light hitting the detector. This is problematic especially when the intensity of the excitation line is many times greater than the intensity of the actual detection light, which is typically the case in fluorescence microscopy. A further disadvantage is that the filtering generally also affects the detection light, thus corrupting the measurement result.

SUMMARY OF THE INVENTION

It is therefore an object of the present invention to provide a device for selectively detecting specific wavelength components of a light beam and a method for suppressing excitation lines in the detection light beam of a microscope in such a manner that the detection of unwanted wavelength components of a light beam to be detected is suppressed to a large extent using a simple and flexible design.

The present invention provides a device for selectively detecting specific wavelength components of a light beam, including an element for spectrally spreading out the light beam and a detector array downstream of the element. The element and the detector array are matched to each other in such a manner that selectable wavelength components of the light beam hit light-insensitive regions of the detector array, and the remaining wavelength components of the light beam hit light-sensitive regions of the detector array.

In accordance with the present invention, it was discovered that in order to avoid detection of unwanted wavelength components of a light beam, it is not absolutely necessary to block the wavelength components from the optical path of the light beam in a complex manner before they reach the detector. Rather, in accordance with the present invention, the element for spectrally spreading out the light beam and the detector in the form of a detector array are matched to each other in such a manner that the unwanted wavelength components hit light-insensitive regions of the detector array. Thus, the present invention takes advantage of the special design of the detector array, which, for manufacturing and functional reasons, has light-insensitive regions between the actual photosensitive regions, i.e., the so-called channels. When these photo-inactive regions are adjusted to coincide with the unwanted wavelength components, these components may thus be easily suppressed during detection.

Specifically, the element for spectral spreading could be, for example, a prism, a grating, or a diffractive optical element, for example, in the form of a hologram. With regard to high-precision adjustment, electro-optical elements or micromechanical scanners have turned out to be advantageous.

A mask could advantageously be disposed in front of the detector array, thus allowing additional photo-inactive regions to be artificially created on the detector array, independently of the specific design of the detector array. Alternatively, or in addition to a mask, a micro-optical element, for example, in the form of a microlens array or a polarization array, could be disposed in front of the detector array.

To increase the variability of the device, provision could be made that the detector array, the mask and/or the micro-optical element be movable independently of each other. In this connection, it is advantageous for the fine adjustment of the individual components if the individual components are movable in three translational and three rotational degrees of freedom.

A specific possible use of the device is, in particular, the use in a fluorescence microscope. In a fluorescence microscope, an excitation light beam of an illumination light source is directed via microscope optics onto a sample from which a detection light beam emanates. In this connection, the excitation light reflected by the sample and contained in the detection light beam could, at least partially, hit light-insensitive regions of the detector array while the fluorescent light produced in the sample hits light-sensitive regions. This allows excitation lines to be excluded from detection in a particularly sophisticated manner.

The present invention also provides a method for suppressing excitation lines in the detection light beam of a microscope, in particular for use in a fluorescence microscope, in which an element for spectrally spreading out the detection light beam and a detector array downstream of the element are disposed in the optical path of the detection light beam. According to the method the element and the detector array are matched to each other in such a manner that the excitation lines at least partially hit light-insensitive regions of the detector array, and the remaining wavelength components of the detection light beam hit light-sensitive regions of the detector array.

In accordance with the present invention, it was discovered that detection of the excitation lines can be avoided by matching the element for spectrally spreading out the detection light beam and the detector array to each other in such a manner that the excitation lines hit light-insensitive regions of the detector array. Thus, the detector array "sees" a reduced light intensity, i.e., essentially only the actual detection light, in particular, fluorescent light, and the number of occurrences of electronic crosstalk between the channels is markedly reduced.

For a given detector array design, the excitation lines could be selected to coincide with the insensitive regions of the detector array. In this connection, the excitation lines could either be separated from a white light source, for example, by filtering, or produced by a tunable laser light source.

For given fixed excitation lines, the matching between the element for spectrally spreading out the detection light beam and the detector array may be accomplished in different ways. For example, if the element for spectral spreading is permanently aligned, it is possible to move the detector array until the excitation lines hit light-insensitive regions of the detector array. Conversely, if the detector array has a given fixed position, it is possible to change the alignment of the element for spectral spreading. Advantageously, the above-mentioned adjustments may be made even during a measurement.

For specific uses, for example, in a microscope having given fixed excitation lines, the detector array could already be manipulated during production in such a manner that light-insensitive regions are produced at the locations that are hit by the excitation lines during later use/measurement.

In order to avoid repetition, reference is also made to the portion of the specification relating to the device according to the present invention.

BRIEF DESCRIPTION OF THE DRAWINGS

The teaching of the present invention can be embodied and refined in different ways. In this regard, on one hand, reference is made to the claims and, on the other hand, to the following description of preferred exemplary embodiments of the present invention with reference to the drawings. In conjunction with the explanation of the preferred exemplary embodiments of the present invention with reference to the drawings, an explanation is also given of generally preferred embodiments and developments of the teaching.

DETAILED DESCRIPTION

Figure 1:
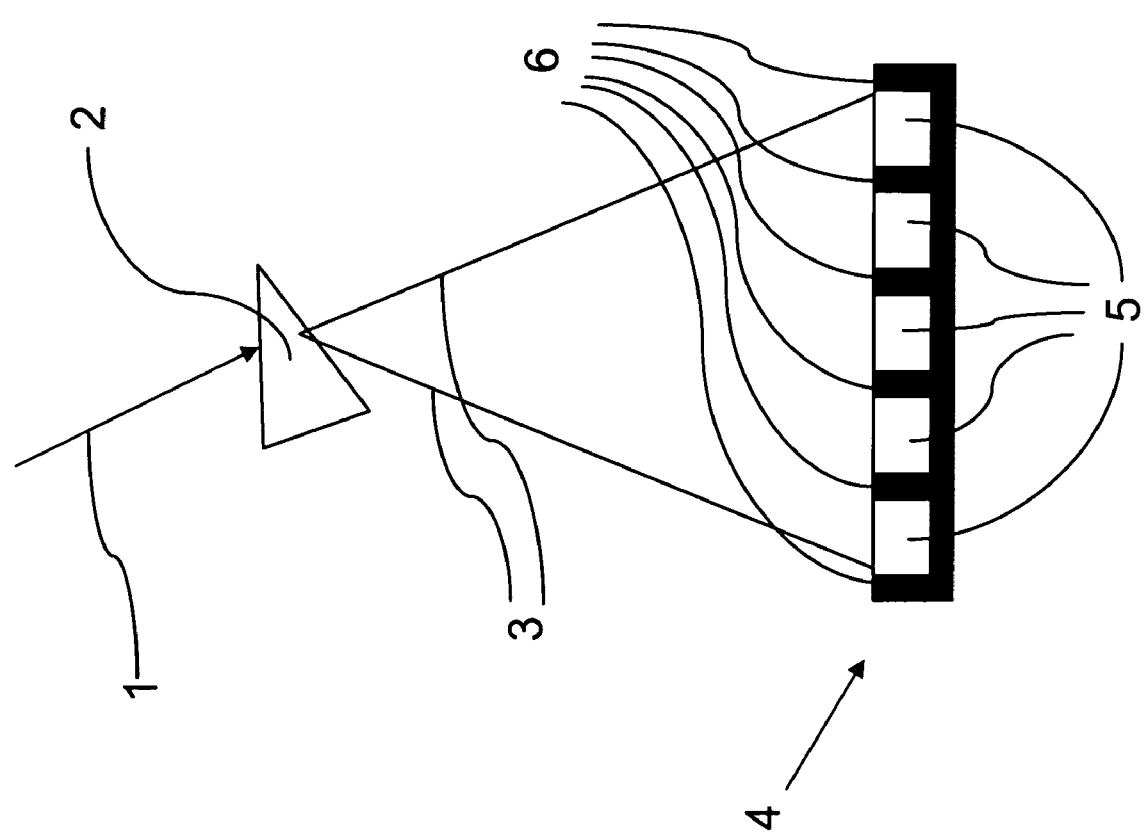
FIG. 1 is a schematic view of a first exemplary embodiment of a device according to the present invention for selectively detecting specific wavelength components of a light beam.

FIG. 1 schematically shows an exemplary embodiment of a device for selectively detecting specific wavelength components of a light beam 1. For spectral spreading, light beam 1 initially passes through a prism 2, and then the spread-out light beam 3 hits a detector array 4. Detector array 4 is a commercial CCD line detector or a commercial PMT array, which have "photo-inactive" regions 6 (shown dark in FIG. 1) between the individual photosensitive regions 5 (channels) shown bright. These regions 6, which are insensitive to light, are basically attributable to the manufacturing process and the design of detector array 4, but may also be artificially created at a later time.

In accordance with the present invention, prism 2 and detector array 4 are matched to each other in such a manner that the wavelength components of light beam 1, 3 that are not to be detected hit insensitive regions 6 of detector array 4 while the remaining wavelength components of light beam 1, 3, which are desired to be detected, hit photosensitive regions 5 of detector array 4.

Figure 2:
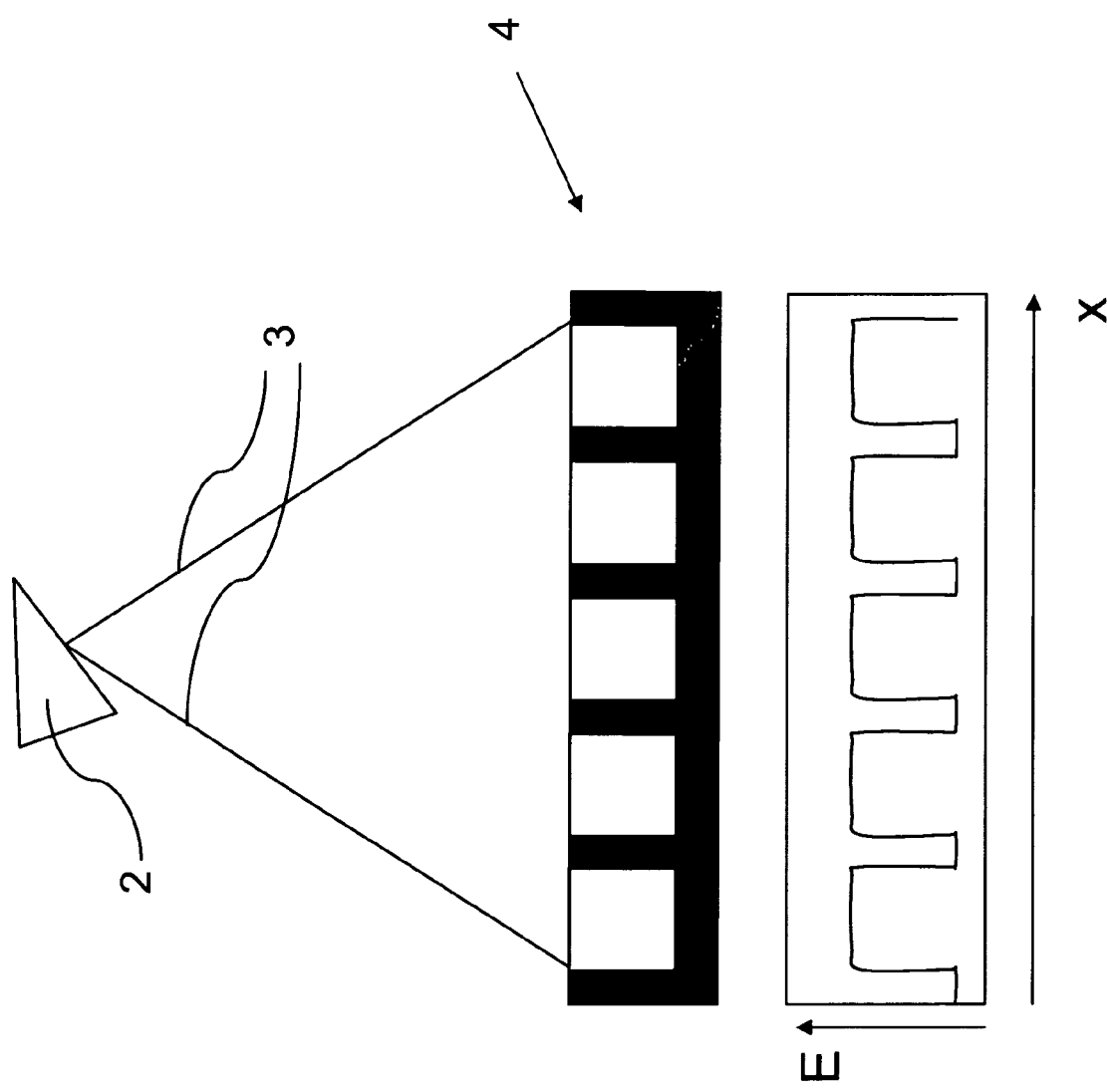
FIG. 2 schematically shows the device of FIG. 1 together with a graph depicting the detection sensitivity along the detector array.

FIG. 2 shows the device of FIG. 1, identical parts being denoted by the same reference numerals. Additionally, sensitivity E, i.e., the photosensitivity is plotted along detector array 4 in a graph. In this connection, the merlon-shaped pattern reflects the structure of detector array 4: The sensitivity in photosensitive regions 5 is high while it is negligible in the insensitive regions 6 between the individual channels 5.

Figure 3:
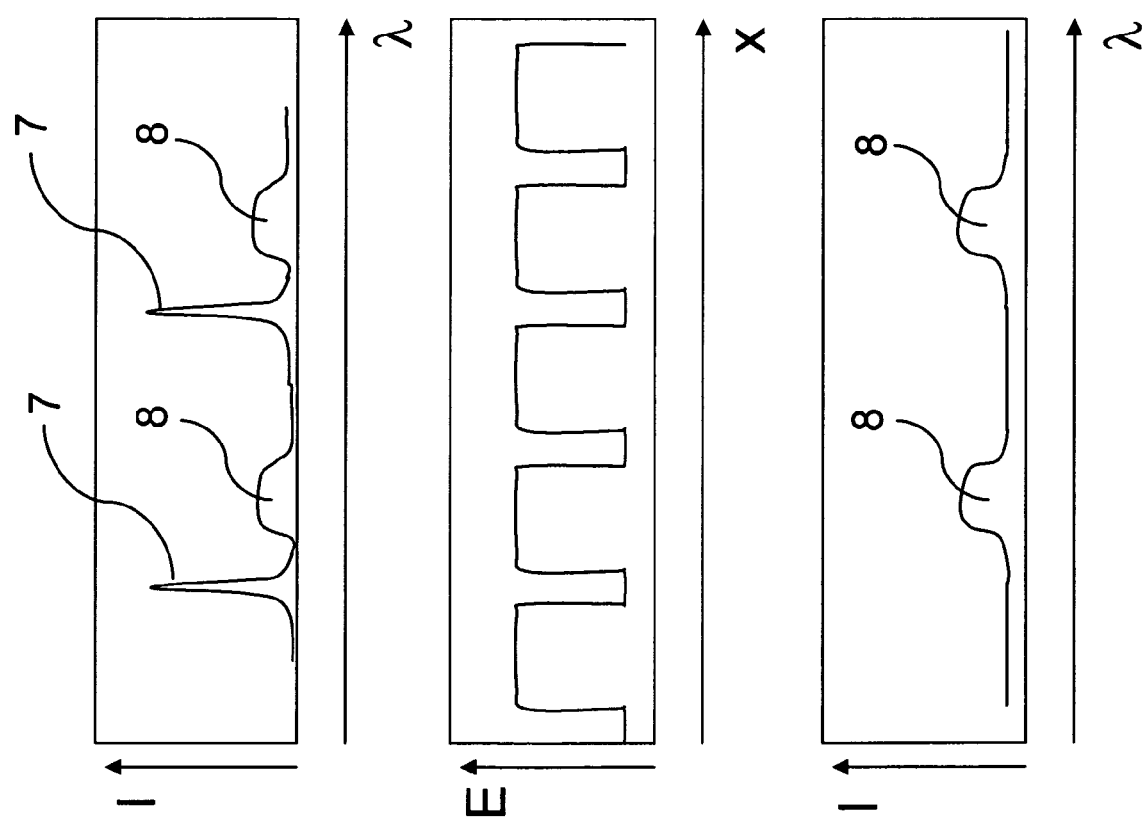
FIG. 3 graphically depicts the result of a convolution of the spectrum of the excitation and fluorescent light with the spatial sensitivity of the detector array.

FIG. 3 shows three diagrams, the upper diagram of which graphically shows a characteristic excitation and fluorescence spectrum as typically occurs in fluorescence microscopy. Shown are two sharp excitation lines 7 that are separated from a white light source by suitable filters, or produced by tunable laser light sources. Fluorescent light 8 emitted by the excited sample is shifted toward higher wavelengths $\lambda$. Clearly discernible is the generally lower intensity I of fluorescent light 8 compared to the intensity of excitation lines 7.

The middle diagram of FIG. 3, in turn, shows sensitivity E along detector array 4. The result of a convolution of the excitation and fluorescent spectrum from the upper diagram with the sensitivity from the middle diagram is shown in the lower diagram. As can easily be seen, the two excitation lines 7 have nearly completely disappeared while the two wavelength regions of fluorescent light 8 are reproduced nearly unchanged. Thus, the measurement result is not disturbed by a plurality of occurrences of electronic crosstalk between the individual channels 5 of detector array 4. Moreover, it is possible to operate detector array 4 in a range far below its saturation threshold, or to increase the excitation intensity so as to perform the measurement with sufficient photon statistics in a shorter time.

Figure 4:
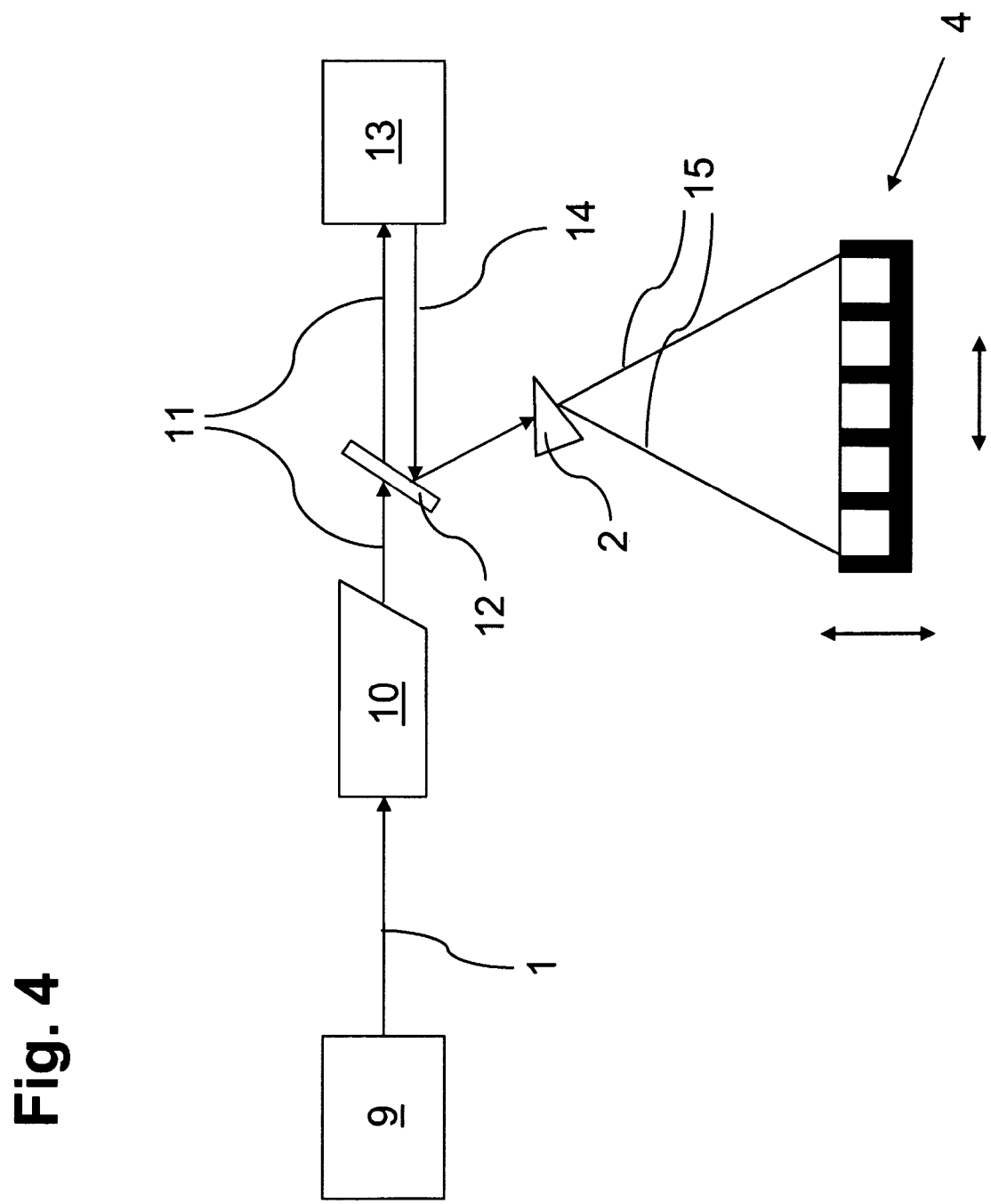
FIG. 4 shows a second exemplary embodiment of a device according to the present invention for use in a fluorescence microscope.

FIG. 4 schematically shows the device according to the present invention in connection with a fluorescence microscope. A light beam 1 emitted by a white light source 9 is directed onto an AOTF (acousto-optical tunable filter) 10. This fast acousto-optical element makes it possible to control the optical power for the incident wavelengths, and thus to generate an excitation light beam 11 having one or more sharp excitation lines. Excitation light beam 11 is directed onto a fluorescent sample 13 via a beam splitter 12 and suitable microscope optics. The microscope optics are sufficiently known to a one skilled in this field, but not shown in FIG. 4 for the sake of clarity.

Detection light beam 14, which contains both fluorescent light produced in sample 13 and excitation light reflected by sample 13, is directed onto a prism 2 via beam splitter 12. Detection light beam 15 spread out by prism 2 hits detector array 4; prism 2 and detector array 4 being matched to each other in an inventive manner such that the excitation lines hit insensitive regions 6 of detector array 4. This matching may be accomplished by moving detector array 4 along the directions indicated by the double arrows. For fine tuning, it is, in principle, conceivable for detector array 4 to be movable in all six degrees of freedom (3 translational, 3 rotational). Matching may be accomplished, in particular, by moving detector array 4, even during a measurement. Additionally or alternatively, the matching may be accomplished by rotating prism 2.

Figure 5:
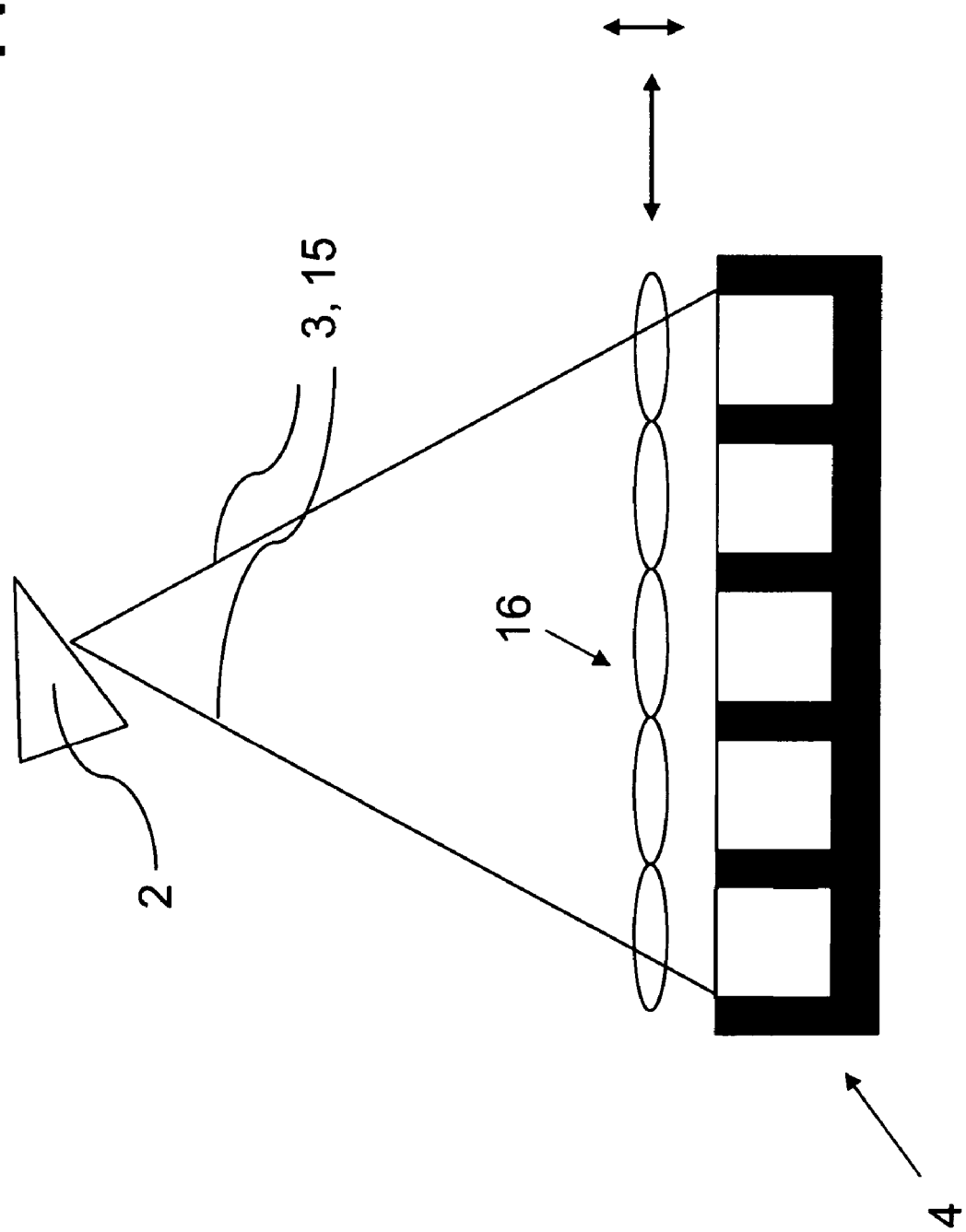
FIG. 5 shows a further exemplary embodiment of a device according to the present invention, in which the insensitive regions of the detector array are matched to the wavelengths of the excitation light using a movable (micro-) lens array.

FIG. 5 schematically shows a device according to the present invention, in which a (micro-) lens array 16 is disposed in front of detector array 4. Lens array 16 is movable in the directions indicated by the double arrows and used for adapting the insensitive regions 6 of detector array 4 to the excitation wavelengths.

Figure 6:
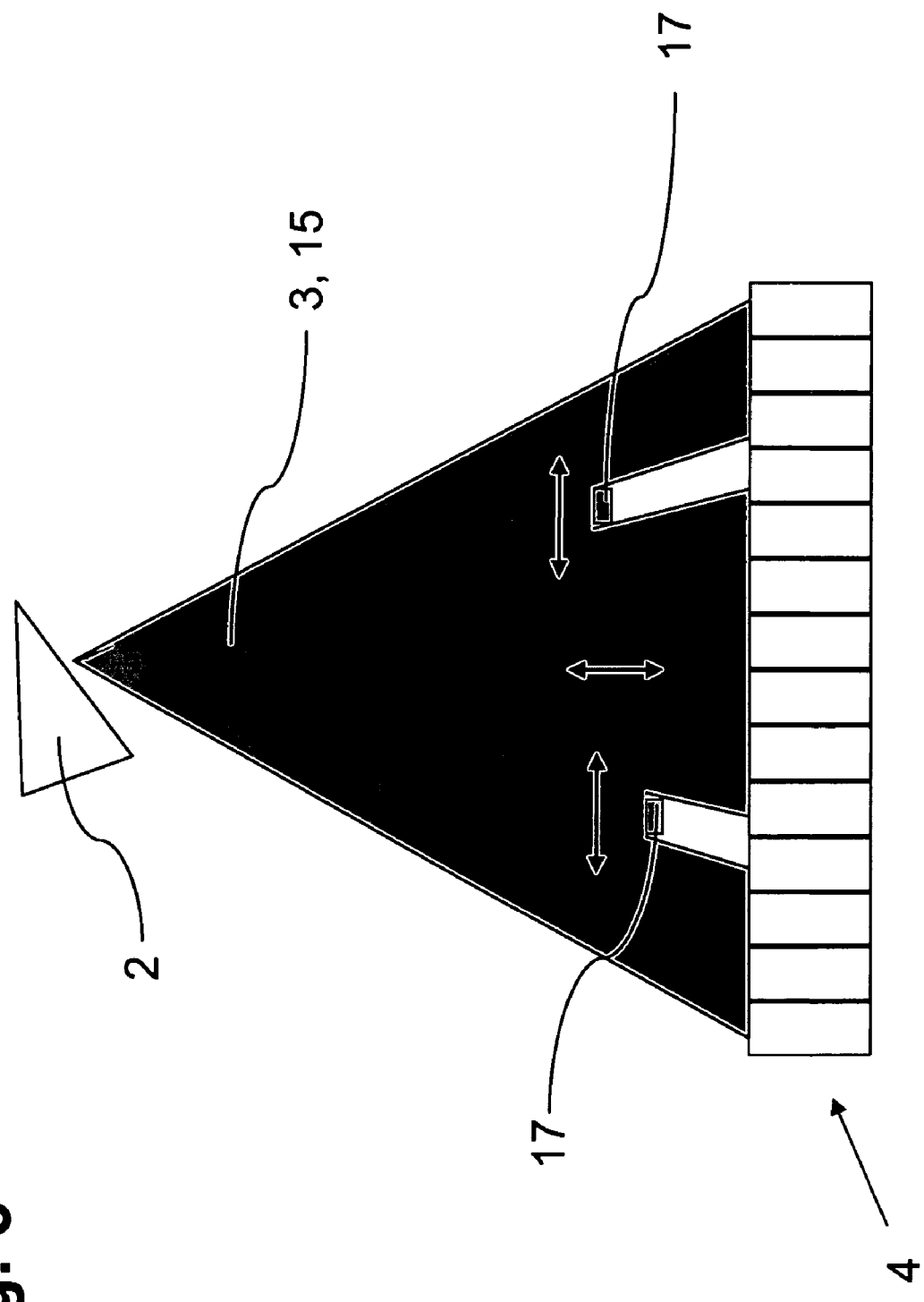
FIG. 6 shows yet another exemplary embodiment of a device according to the present invention, in which the insensitive regions of the detector array and the discrete wavelengths of an excitation light source are matched using movable masks.

Finally, FIG. 6 schematically shows a device according to the present invention, in which the matching between prism 2 and detector array 4 can be accomplished using movable masks 17. Masks 17 can be moved parallel to the surface of detector array 4 along the directions indicated by the double arrows, and artificially create insensitive detector regions 6. The nearer mask 17 is to the surface of detector array 4, the narrower is the spectral region blocked by mask 17. This means that in order to block an unsharp, i.e., broad excitation line, the respective mask 17 must be disposed at a correspondingly larger distance from the surface of detector array 4.

To conclude, it should be pointed out very particularly that the exemplary embodiments discussed above serve only to illustrate the claimed teaching without limiting it to the exemplary embodiments.

What is claimed is:

1. A device for selectively detecting specific wavelength components of a light beam, the device comprising:
   an illumination light source configured to provide an excitation light beam including excitation light capable of producing fluorescence in a sample;
   microscope optics configured to direct the excitation light beam onto the sample so as to provide a detection light beam including light of the excitation light reflected by the sample and fluorescent light produced in the sample;
   a spectral spreading element configured to spectrally spread the detection light beam; and
   a detector array disposed downstream of the element, the detector array including a light-insensitive region and a light-sensitive region;
   wherein the spectral spreading element and the detector array are matched to each other so that, without use of a filter or blocking device, a selectable wavelength component of the detection light beam having a wavelength of the excitation light hits the light-insensitive region and a remaining wave length component of the detection light beam having a wavelength of the fluorescent light hits the light-sensitive region.

2. The device as recited in claim 1 wherein the spectral spreading element includes at least one of a prism, a grating, and a diffractive optical element.

3. The device as recited in claim 1 wherein the spectral spreading element includes at least one of an electro-optical element and a mechanical scanner.

4. The device as recited in claim 3 wherein the mechanical scanner includes a micro-mechanical scanner.

5. A method for suppressing excitation lines in a detection light beam of a microscope, the method comprising:
   producing fluorescence in a sample using at least a first excitation line of the excitation lines;
   providing a detection light beam including the first excitation line and fluorescent light from the sample;
   providing a spectral spreading element disposed in an optical path of the detection light beam and configured to spectrally spreading the detection light beam;
   providing a detector array disposed in the optical path of the spectrally spread detection light beam downstream of the spectral spreading element, the detector array including a light-insensitive region and a light-sensitive region; and
   matching the spectral spreading element and the detector array to each other so that, without use of a filter or blocking device, the first excitation line at least partially hits the light-insensitive region and a remaining wavelength component of the detection light beam having a wavelength of the fluorescent light hits the light-sensitive region.

6. The method as recited in claim 5 wherein the microscope is a fluorescence microscope.

7. The method as recited in claim 5 further comprising selecting the first excitation line according to the design of the detector array so that the first excitation line coincides with the light-insensitive region.

8. The method as recited in claim 7 further comprising producing the first excitation line by at least one of separation from a white light source and by emission from a tunable laser light source.

9. The method as recited in claim 5 further comprising moving the detector array so that the first excitation line coincides with the light-insensitive region.

10. The method as recited in claim 5 wherein the matching is performed by manufacturing the detector array so that the light-insensitive region is disposed so as to be hit by the first excitation line.

* * * * *